(12) United States Patent
Howard et al.

(10) Patent No.: US 7,931,987 B2
(45) Date of Patent: *Apr. 26, 2011

(54) LITHIUM-ION BATTERY

(75) Inventors: William G. Howard, Roseville, MN (US); Craig L. Schmidt, Eagan, MN (US); Erik R. Scott, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/789,149

(22) Filed: May 27, 2010

(65) Prior Publication Data
US 2010/0239908 A1 Sep. 23, 2010

Related U.S. Application Data

(62) Division of application No. 12/429,061, filed on Apr. 23, 2009, now Pat. No. 7,740,985, which is a division of application No. 10/978,617, filed on Oct. 29, 2004, now Pat. No. 7,563,541.

(51) Int. Cl.
*H01M 4/58* (2010.01)
(52) U.S. Cl. .......... 429/231.1; 429/231.5; 429/217; 429/245; 429/233; 429/247; 429/249; 429/94; 429/129; 429/322; 429/324; 429/323
(58) Field of Classification Search .......... 429/231.3, 429/231.1, 231.5, 217, 245, 233, 247, 249, 429/94, 129, 322, 324, 323
See application file for complete search history.

(56) References Cited

U.S. PATENT DOCUMENTS

| | | | |
|---|---|---|---|
| 3,462,303 | A | 8/1969 | Reber |
| 3,791,867 | A | 2/1974 | Broadhead et al. |
| 3,864,167 | A | 2/1975 | Broadhead et al. |
| 3,898,096 | A | 8/1975 | Heredy et al. |
| 4,009,052 | A | 2/1977 | Whittingham |
| 4,048,397 | A | 9/1977 | Rothbauer |
| 4,049,887 | A | 9/1977 | Whittingham |
| 4,113,921 | A | 9/1978 | Goldstein et al. |
| 4,194,062 | A | 3/1980 | Carides et al. |
| 4,202,702 | A | 5/1980 | Nuss |
| 4,340,652 | A | 7/1982 | Raistrick et al. |
| 4,446,212 | A | 5/1984 | Kaun |

(Continued)

FOREIGN PATENT DOCUMENTS
EP 0 732 761 A2 9/1996
(Continued)

OTHER PUBLICATIONS

Ariyoshi et al., "Three-Volt Lithium-Ion Battery with Li[Ni1/2Mn3/2]O4 and the Zero-Strain Insertion Material of Li[Li1/3Ti5/3]O4", Journal of Power Sources, 119-121, 2003, pp. 959-963.

(Continued)

*Primary Examiner* — Laura S Weiner
(74) *Attorney, Agent, or Firm* — Scott A. Marks; Foley & Lardner LLP

(57) ABSTRACT

A lithium-ion battery includes a positive electrode comprising a current collector and a first active material comprising $LiCoO_2$ and a negative electrode comprising a current collector, a second active material, and a third active material. The second active material comprises a lithium titanate material and the third active material is $V_2O_5$. The third active material exhibits charging and discharging capacity below a corrosion potential of the current collector of the negative electrode and above a decomposition potential of the first active material.

33 Claims, 6 Drawing Sheets

U.S. PATENT DOCUMENTS

| | | |
|---|---|---|
| 4,464,447 A | 8/1984 | Lazzari et al. |
| 4,507,371 A | 3/1985 | Thackeray et al. |
| 4,547,442 A | 10/1985 | Besenhard et al. |
| 4,555,456 A | 11/1985 | Kanehori et al. |
| 4,668,595 A | 5/1987 | Yoshino et al. |
| 4,764,437 A | 8/1988 | Kaun |
| 4,830,939 A | 5/1989 | Lee et al. |
| H723 H | 1/1990 | Plichta et al. |
| 5,053,297 A | 10/1991 | Yamahira et al. |
| 5,077,151 A | 12/1991 | Yasuda et al. |
| 5,147,737 A | 9/1992 | Post et al. |
| 5,147,739 A | 9/1992 | Beard |
| 5,160,712 A | 11/1992 | Thackeray et al. |
| 5,162,170 A | 11/1992 | Miyabayashi et al. |
| 5,162,178 A | 11/1992 | Ohsawa et al. |
| 5,169,736 A | 12/1992 | Bittihn et al. |
| 5,176,969 A | 1/1993 | Miyabayashi et al. |
| 5,187,033 A | 2/1993 | Koshiba |
| 5,187,035 A | 2/1993 | Miyabayashi et al. |
| 5,196,279 A | 3/1993 | Tarascon |
| 5,264,201 A | 11/1993 | Dahn et al. |
| 5,284,721 A | 2/1994 | Beard |
| 5,296,318 A | 3/1994 | Gozdz et al. |
| 5,300,373 A | 4/1994 | Shackle |
| 5,322,746 A | 6/1994 | Wainwright |
| 5,340,666 A | 8/1994 | Tomantschger et al. |
| 5,401,598 A | 3/1995 | Miyabayashi et al. |
| 5,411,537 A | 5/1995 | Munshi et al. |
| 5,418,090 A | 5/1995 | Koksbang et al. |
| 5,498,489 A | 3/1996 | Dasgupta et al. |
| 5,510,212 A | 4/1996 | Delnick et al. |
| 5,525,441 A | 6/1996 | Reddy et al. |
| 5,545,468 A | 8/1996 | Koshiba et al. |
| 5,547,785 A | 8/1996 | Yumiba et al. |
| 5,569,553 A | 10/1996 | Smesko et al. |
| 5,576,608 A | 11/1996 | Nagai et al. |
| 5,652,072 A | 7/1997 | Lamanna et al. |
| 5,670,862 A | 9/1997 | Lewyn |
| 5,691,081 A | 11/1997 | Krause et al. |
| 5,744,258 A | 4/1998 | Bai et al. |
| 5,744,264 A | 4/1998 | Barker |
| 5,776,628 A | 7/1998 | Kraft et al. |
| 5,882,218 A | 3/1999 | Reimers |
| 5,888,665 A | 3/1999 | Bugga et al. |
| 5,891,592 A | 4/1999 | Mao et al. |
| 5,911,947 A | 6/1999 | Mitchell |
| 5,935,724 A | 8/1999 | Spillman et al. |
| 5,935,728 A | 8/1999 | Spillman et al. |
| 5,968,681 A | 10/1999 | Miura et al. |
| 6,001,139 A | 12/1999 | Asanuma et al. |
| 6,001,507 A | 12/1999 | Ono et al. |
| 6,007,947 A | 12/1999 | Mayer |
| 6,022,643 A | 2/2000 | Lee et al. |
| 6,025,093 A | 2/2000 | Herr |
| 6,060,186 A | 5/2000 | Broussely |
| 6,067,474 A | 5/2000 | Schulman et al. |
| 6,120,938 A | 9/2000 | Atsumi et al. |
| 6,139,815 A | 10/2000 | Atsumi et al. |
| 6,165,638 A | 12/2000 | Spillman et al. |
| 6,165,646 A | 12/2000 | Takada et al. |
| 6,171,729 B1 | 1/2001 | Gan et al. |
| 6,203,947 B1 | 3/2001 | Peled et al. |
| 6,203,994 B1 | 3/2001 | Epps et al. |
| 6,207,327 B1 | 3/2001 | Takada et al. |
| 6,221,531 B1 | 4/2001 | Vaughey et al. |
| 6,228,536 B1 | 5/2001 | Wasynczuk |
| 6,258,473 B1 | 7/2001 | Spillman et al. |
| 6,265,100 B1 | 7/2001 | Saaski et al. |
| 6,274,271 B1 | 8/2001 | Koshiba et al. |
| 6,287,721 B1 | 9/2001 | Xie et al. |
| 6,316,145 B1 | 11/2001 | Kida et al. |
| 6,335,115 B1 | 1/2002 | Meissner |
| 6,352,798 B1 | 3/2002 | Lee et al. |
| 6,365,301 B1 | 4/2002 | Michot et al. |
| 6,372,384 B1 | 4/2002 | Fujimoto et al. |
| 6,379,842 B1 | 4/2002 | Mayer |
| 6,451,480 B1 | 9/2002 | Gustafson et al. |
| 6,453,198 B1 | 9/2002 | Torgerson et al. |
| 6,461,751 B1 | 10/2002 | Boehm et al. |
| 6,461,757 B1 | 10/2002 | Sasayama et al. |
| 6,475,673 B1 | 11/2002 | Yamawaki et al. |
| 6,489,062 B1 | 12/2002 | Watanabe et al. |
| 6,503,662 B1 | 1/2003 | Hamamoto et al. |
| 6,528,208 B1 | 3/2003 | Thackeray et al. |
| 6,553,263 B1 | 4/2003 | Meadows et al. |
| 6,596,439 B1 | 7/2003 | Tsukamoto et al. |
| 6,605,382 B2 | 8/2003 | Ruth et al. |
| 6,645,670 B2 | 11/2003 | Gan |
| 6,645,675 B1 | 11/2003 | Munshi |
| 6,673,493 B2 | 1/2004 | Gan et al. |
| 6,677,083 B2 | 1/2004 | Suzuki et al. |
| 6,706,445 B2 | 3/2004 | Barker et al. |
| 6,720,112 B2 | 4/2004 | Barker et al. |
| 6,730,437 B2 | 5/2004 | Leising et al. |
| 6,737,191 B2 | 5/2004 | Gan et al. |
| 6,759,168 B2 | 7/2004 | Yamasaki et al. |
| 6,761,744 B1 | 7/2004 | Tsukamoto et al. |
| 6,777,132 B2 | 8/2004 | Barker et al. |
| 6,824,920 B1 | 11/2004 | Iwamoto et al. |
| 6,841,304 B2 | 1/2005 | Michot et al. |
| 6,849,360 B2 | 2/2005 | Marple |
| 6,905,795 B2 | 6/2005 | Jung et al. |
| 6,905,796 B2 | 6/2005 | Ishida et al. |
| 6,908,711 B2 | 6/2005 | Fauteux et al. |
| 6,942,949 B2 | 9/2005 | Besenhard et al. |
| 7,018,743 B2 | 3/2006 | Guidi et al. |
| 7,029,793 B2 | 4/2006 | Nakagawa et al. |
| 7,101,642 B2 | 9/2006 | Tsukamoto et al. |
| 7,157,185 B2 | 1/2007 | Marple |
| 7,177,691 B2 | 2/2007 | Meadows et al. |
| 7,184,836 B1 | 2/2007 | Meadows et al. |
| 7,191,008 B2 | 3/2007 | Schmidt et al. |
| 7,202,000 B2 | 4/2007 | Iriyama et al. |
| 7,211,350 B2 | 5/2007 | Amatucci |
| 7,337,010 B2 | 2/2008 | Howard et al. |
| 7,341,803 B2 | 3/2008 | Huang et al. |
| 7,459,235 B2 | 12/2008 | Choi et al. |
| 7,524,580 B1 | 4/2009 | Birke et al. |
| 7,541,114 B2 | 6/2009 | Ohzuku et al. |
| 7,563,541 B2 | 7/2009 | Howard et al. |
| 7,582,380 B1 | 9/2009 | Dunstan et al. |
| 7,582,387 B2 | 9/2009 | Howard et al. |
| 7,740,985 B2 | 6/2010 | Howard |
| 7,799,470 B2 | 9/2010 | Cho et al. |
| 7,807,299 B2 | 10/2010 | Howard et al. |
| 7,818,068 B2 | 10/2010 | Meadows et al. |
| 2001/0008725 A1 | 7/2001 | Howard |
| 2001/0012590 A1 | 8/2001 | Ehrlich |
| 2001/0021472 A1 | 9/2001 | Barker et al. |
| 2001/0031401 A1 | 10/2001 | Yamawaki et al. |
| 2003/0025482 A1 | 2/2003 | Tsukamoto et al. |
| 2003/0104282 A1 | 6/2003 | Xing et al. |
| 2003/0124423 A1 | 7/2003 | Sasaki et al. |
| 2003/0129485 A1 | 7/2003 | Guidi et al. |
| 2003/0157410 A1 | 8/2003 | Jarvis et al. |
| 2003/0215716 A1 | 11/2003 | Suzuki et al. |
| 2004/0023117 A1 | 2/2004 | Imachi et al. |
| 2004/0062989 A1 | 4/2004 | Ueno et al. |
| 2004/0072072 A1 | 4/2004 | Suzuki et al. |
| 2004/0096745 A1 | 5/2004 | Shibano et al. |
| 2004/0147971 A1 | 7/2004 | Greatbatch et al. |
| 2004/0147972 A1 | 7/2004 | Greatbatch et al. |
| 2004/0158296 A1 | 8/2004 | Greatbatch et al. |
| 2004/0168307 A1 | 9/2004 | Hong |
| 2004/0176818 A1 | 9/2004 | Wahlstrand et al. |
| 2004/0197657 A1 | 10/2004 | Spitler et al. |
| 2004/0209156 A1 | 10/2004 | Ren et al. |
| 2005/0031919 A1 | 2/2005 | Ovshinsky et al. |
| 2005/0069777 A1 | 3/2005 | Takami et al. |
| 2005/0130043 A1 | 6/2005 | Gao et al. |
| 2005/0147889 A1 | 7/2005 | Ohzuku et al. |
| 2005/0164082 A1 | 7/2005 | Kishi et al. |
| 2005/0244716 A1 | 11/2005 | Ogawa et al. |
| 2006/0024582 A1 | 2/2006 | Li et al. |
| 2006/0046149 A1 | 3/2006 | Yong et al. |
| 2006/0068282 A1 | 3/2006 | Kishi et al. |
| 2006/0093871 A1 | 5/2006 | Howard et al. |

| | | | |
|---|---|---|---|
| 2006/0093872 A1 | 5/2006 | Howard et al. | |
| 2006/0093873 A1 | 5/2006 | Howard et al. | |
| 2006/0093894 A1 | 5/2006 | Scott et al. | |
| 2006/0093913 A1 | 5/2006 | Howard et al. | |
| 2006/0093917 A1 | 5/2006 | Howard et al. | |
| 2006/0093921 A1 | 5/2006 | Scott et al. | |
| 2006/0093923 A1 | 5/2006 | Howard et al. | |
| 2006/0095094 A1 | 5/2006 | Howard et al. | |
| 2006/0216612 A1 | 9/2006 | Jambunathan et al. | |
| 2006/0234125 A1 | 10/2006 | Valle | |
| 2006/0251968 A1 | 11/2006 | Tsukamoto et al. | |
| 2007/0009801 A1 | 1/2007 | Inagaki et al. | |
| 2007/0059587 A1 | 3/2007 | Kishi et al. | |
| 2007/0072085 A1 | 3/2007 | Chen et al. | |
| 2007/0077496 A1 | 4/2007 | Scott et al. | |
| 2007/0111099 A1 | 5/2007 | Nanjundaswamy et al. | |
| 2007/0134556 A1 | 6/2007 | Sano et al. | |
| 2007/0162083 A1 | 7/2007 | Schmidt et al. | |
| 2007/0233195 A1 | 10/2007 | Wahlstrand et al. | |
| 2007/0239221 A1 | 10/2007 | Kast et al. | |
| 2007/0248881 A1 | 10/2007 | Scott et al. | |
| 2007/0284159 A1 | 12/2007 | Takami et al. | |
| 2008/0020278 A1 | 1/2008 | Schmidt et al. | |
| 2008/0020279 A1 | 1/2008 | Schmidt et al. | |
| 2008/0026297 A1 | 1/2008 | Chen et al. | |
| 2008/0044728 A1 | 2/2008 | Schmidt et al. | |
| 2009/0035662 A1 | 2/2009 | Scott et al. | |
| 2009/0274849 A1 | 11/2009 | Scott et al. | |
| 2009/0286151 A1 | 11/2009 | Scott | |
| 2009/0286158 A1 | 11/2009 | Howard | |
| 2010/0009245 A1 | 1/2010 | Howard | |
| 2010/0015528 A1 | 1/2010 | Howard | |
| 2010/0076523 A1 | 3/2010 | Howard | |

FOREIGN PATENT DOCUMENTS

| | | | |
|---|---|---|---|
| EP | 0 982 790 A1 | 3/1998 | |
| EP | 1 014 465 A1 | 6/2000 | |
| EP | 1 018 773 A1 | 7/2000 | |
| EP | 1 069 635 A1 | 1/2001 | |
| EP | 0 567 149 B1 | 11/2001 | |
| EP | 1 282 180 A1 | 2/2003 | |
| EP | 1 487 039 A1 | 12/2004 | |
| EP | 1 722 439 A1 | 11/2006 | |
| JP | 56-136462 A | 10/1981 | |
| JP | 57-011476 A | 1/1982 | |
| JP | 63-001708 B2 | 1/1982 | |
| JP | 57-152669 A | 9/1982 | |
| JP | 02309568 A | 12/1990 | |
| JP | 06275263 A | 9/1994 | |
| JP | 10027626 A | 1/1998 | |
| JP | 2000-156229 A | 6/2000 | |
| JP | 2000-195499 A | 7/2000 | |
| JP | 2001-126756 A | 5/2001 | |
| JP | 2001-185141 A | 7/2001 | |
| WO | WO-97/06569 A1 | 2/1997 | |
| WO | WO-97/48141 A1 | 12/1997 | |
| WO | WO-00/17950 A1 | 3/2000 | |
| WO | WO 01/33656 A1 | 5/2001 | |
| WO | WO-02/09215 A2 | 1/2002 | |
| WO | WO-02/21628 A1 | 3/2002 | |
| WO | WO-02/39524 A1 | 5/2002 | |
| WO | WO-02/069414 A2 | 9/2002 | |
| WO | WO-02/095845 A1 | 11/2002 | |
| WO | WO-03/044880 A1 | 5/2003 | |
| WO | WO-03/075371 A2 | 9/2003 | |
| WO | WO-03/075376 A1 | 9/2003 | |
| WO | WO-03/090293 A2 | 10/2003 | |
| WO | WO-2006/050022 A2 | 5/2006 | |
| WO | WO-2006/050023 A2 | 5/2006 | |
| WO | WO-2006/050098 A1 | 5/2006 | |
| WO | WO-2006/050099 A1 | 5/2006 | |
| WO | WO-2006/050100 A2 | 5/2006 | |
| WO | WO-2006/050117 A2 | 5/2006 | |
| WO | WO-2006/064344 A2 | 6/2006 | |

OTHER PUBLICATIONS

"Battery Materials—Ceramic Anode Material for 2.4 V Lithium-Ion Batteries"—EXM 1037—Li4Ti5O12 (1 page), available at least by Oct. 25, 2004.

Belharouak et al., "On the Safety of the Li4Ti5O12/LiMn2O4 Lithium-Ion Battery System," (ECS) Journal of the Electrochemical Society, vol. 154, No. 12, 2007, pp. A1083-A1087.

Brohan et al., Properties Physiques Des Bronzes MxTiO2(B), Solid State Ionics, vols. 9 and 10, 1983, © North Holland Publishing Company, pp. 419-424.

Cava et al., The Crystal Structures of the Lithium-Inserted Metal Oxides Li0.5TiO2 Anatase, LiTi2O4 Spinel, and Li2Ti2O4, Journal of Solid State Chemistry, vol. 53, Jan. 1984 © Academic Press, Inc., pp. 64-75.

Christensen et al., "Optimization of Lithium Titanate Electrodes for High-Power Cells," (ECS) Journal of the Electrochemical Society, 2006, pp. A560-A565, vol. 153, No. 3.

Colbow et al., Structure and Electrochemistry of the Spinel Oxides LiTi2O4 and Li4/3Ti5/3O4, Journal of Power Sources, vol. 26, 1989, © Elsevier Sequoia, pp. 397-402.

Dahn et al., "Combinatorial Study of Sn1-xCox (0<x<0.6) and [Sn0.55Co0.45]1-yCy (0<y<0.5) Alloy Negative Electrode Materials for Li-Ion Batteries," Journal of Electrochemical Society, vol. 153, 2006, pp. A361-365.

Fauteux et al., "Rechargeable lithium battery anodes: alternatives to metallic lithium," Journal of Applied Electrochemistry, vol. 23, 1993, pp. 1-10.

Ferg et al., "Spinel Anodes for Lithium-Ion Batteries", J. Electrochem. Soc. vol. 141 #11, 1994, pp. L147-L150.

FMC Lithium, CAS No. 74389-93-2, "Stabilized Lithium Metal Powder" Product Specification, Copyright 2001 FMC Corporation, 2 pages.

Guerfi, et al., "Nano Electronically Conductive Titanium-Spinel as Lithium Ion Storage Negative Electrode", Journal of Power Sources, 126, 2004, pp. 163-168.

Guyomard et al., "New amorphous oxides as high capacity negative electrodes for lithium 6 batteries the LixMV04 (M=Ni, Co, Cd, Zn; 1<x<8) series," Journal of Power Sources, vol. 68, 1997, pp. 692-697.

Jansen et al., "Development of a High-Power Lithium-Ion Battery", Journal of Power Sources, 81-82, 1999, pp. 902-905.

Jarvis et al., "A Li-Ion Cell Containing a Non-Lithiated Cathode", Abs. 182, IMLB 12 Meeting, 1 page.

Kavan et al., Proof of Concept—Li4Ti5O12, Electrochemical and Solid State Letters, 2002, vol. 5, A39-A42, p. 13.

Linden, Editor in Chief, Handbook of Batteries, Second Edition, McGraw-Hill, NY, 1995, 6 pages.

Mikula et al., Photoelectrochemical Properties of Anodic TiO2 Layers Prepared by Various Current Densities, J. Electrochemical Society, vol. 139, No. 12, Dec. 1992 © The Electrochemical Society, Inc., pp. 3470-3474.

Murphy et al., "Topochemical Reactions of Rutile Related Structures with Lithium", Mat. Res. Bull, vol. 13, No. 12, 1978, © Pergamon Press, Inc., pp. 1395-1402.

Murphy et al., Lithium Insertion in Anatase: A New Route to the Spinel LiTi2O4, Revue De Chimie Minerale, vol. 19, 1982, 9 pages.

Murphy et al., Ternary LixTiO2 Phases from Insertion Reactions, Solid State Ionics, vols. 9 & 10, 1983 © North-Holland Publishing Company, pp. 413-418.

Nakahara, et al., "Preparation of Particulate Li4Ti5O12 Having Excellent Characteristics as an Electrode Active Material for Power Storage Cells", Journal of Power Sources, 117, 2003, pp. 131-136.

New Li4Ti5O12 Anode Material of Süd-Chemie AG for Lithium Ion Batteries, Süd-Chemie EXM 1037—Li4Ti5O12 , Product Specification, 2 pages.

Ohzuku et al., "Why transition metal (di)oxides are the most attractive materials for batteries," Solid State Ionics, vol. 69, 1994, pp. 201-211.

Ohzuku et al., "Lithium-Ion Batteries of Li[Li1/3Ti5/3]O4 With Selected Positive-Electrode Materials for Long-Life Power Application", Abs. 23, IMLB 12 Meeting, 1 page.

Ohzuku et al., Zero-Strain Insertion Material of Li[Li1/3Ti5/3]O4 for Rechargeable Lithium Cells, Electrochemical Science and Technology, J. Electrochem Soc., vol. 142, No. 5, May 1995 © The Electrochemical Society, Inc., 5 pages.

Ohzuku, Extended Abstracts from the Seventh Int'l Meeting on Li Batteries, Boston, MA, May 15-20, 1994, pp. 111-112.

Peramunage et al., Preparation of Micro-Sized Li4Ti5O12 and Its Electrochemistry in Polyacrylonitrile Electrolye-Based Lithium Cells, Technical Papers, Electrochemical Science and Technology, J. Electrochem Soc., vol. 145, No. 8, Aug. 1998 © The Electrochemical Society, Inc., 7 pages.

Poizot et al., "Nano-sized transition-metal oxides as negative-electrode materials for lithium-ion batteries," Nature, vol. 407, 2000, cover and pp. 496-499.

Prosini et al., "Li4Ti5O12 As Anode in All-Solid-State, Plastic, Lithium-Ion Batteries for Low-Power Applications" Solid State Ionics, 144, 2001, pp. 185-192.

Sasaki et al., Layered Hydrous Titanium Dioxide: Potassium Ion Exchange and Structural Characterization, Inorganic Chemistry, vol. 24, No. 14, © 1985 American Chemical Society, pp. 2265-2271.

Sawai et al., Factors Affecting Rate Capability of a Lithium-ion Battery with Li[Li1/3Ti5/3]04 and LiCo1/2Ni1/2O2, Abs. 75, 205th Meeting, 1 page.

Scrosati, "Low Voltage Lithium-Ion Cells", Advances in Lithium-Ion Batteries Kluwer Academic/Plenum Publishers, pp. 289-308.

Singhal et al., "Nanostructured Electrodes for Next Generation Rechargeable Electrochemical Devices", Journal of Power Sources, 129, 2004, pp. 38-44.

Sun et al., "The Compatibility of a Boron-Based Anion Receptor with the Carbon Anode in Lithium-Ion Batteries," (ECS) Electrochemical and Solid-State Letters, 2003, pp. A43-A46, vol. 6, No. 2.

Sun et al., "Using a Boron-Based Anion Receptor Additive to Improve the Thermal Stability of LiPF6-Based Electrolyte for Lithium Batteries," (ECS) Electrochemical and Solid-State Letters, 2002, pp. A248-A251, vol. 5, No. 11.

Trifonova et al., "Sn-Sb and Sn-Bi Alloys as Anode Materials for Lithium-Ion Batteries," Ionics, vol. 8, 2002, cover and pp. 321-328.

Wang et al., Li Insertion and Ion Exchange Reactions in the Ionic Conducting TI2(M,Ti)8O16 Phases with Hollandite-Type Structure, Technical Papers, Solid-State Science and Technology, J. Electrochem Soc., vol. 138, No. 1, Jan. 1991, © The Electrochemical Society, Inc., pp. 166-172.

Wang et al., Novel Eletrolytes for Nanocrystalline Li4Ti5O12 Based High Power Lithium Ion Batteries, 1 page.

Winter et al., "Insertion Electrode Materials for Rechargeable Lithium Batteries," Advanced Materials, vol. 10, 1998, pp. 725-763.

Winter et al., "Electrochemical lithiation of tin and tin-based intermetallics and composites," Electrochimica Acta, vol. 45, 1999, pp. 31-50.

Zaghib et al., "Electrochemical Study of Li4Ti5O12 As Negative Electrode for Li-Ion Polymer Rechargeable Batteries", Journal of Power Sources, 81-82, 1999, pp. 300-305.

Advisory Action for U.S. Appl. No. 10/978,680, dated Jun. 24, 2010, 3 pages.

Amendment and Reply and Drawings for U.S. Appl. No. 10/978,680, filed Jan. 13, 2010, 19 pages.

Amendment and Reply for U.S. Appl. No. 10/978,680, filed Jan. 25, 2008, 11 pages.

Amendment and Reply for U.S. Appl. No. 10/978,680, filed May 23, 2008, 14 pages.

Amendment and Reply for U.S. Appl. No. 10/978,617, filed Jul. 2, 2008, 9 pages.

Amendment and Reply for U.S. Appl. No. 10/978,617, filed Dec. 11, 2008, 11 pages.

Amendment and Reply for U.S. Appl. No. 10/978,680, filed Jan. 20, 2009, 15 pages.

Amendment and Reply for U.S. Appl. No. 10/978,680, filed Jun. 26, 2009, 19 pages.

Amendment and Reply for U.S. Appl. No. 12/429,061, filed Feb. 15, 2010, 8 pages.

Amendment and Reply for U.S. Appl. No. 10/978,680, filed Jun. 11, 2010, 18 pages.

Final Office Action for U.S. Appl. No. 10/978,680, dated Jul. 9, 2008, 16 pages.

Final Office Action for U.S. Appl. No. 10/978,680, dated Apr. 13, 2010, 23 pages.

International Search Report and Written Opinion for Application No. PCT/US2008/066803, date of mailing Oct. 7, 2008, 12 pages.

International Search Report and Written Opinion for Application No. PCT/US2008/066801, date of mailing Oct. 29, 2008, 10 pages.

International Search Report and Written Opinion for Application No. PCT/US2008/066809, mailing date Oct. 29, 2008, 8 pages.

International Search Report and Written Opinion for International Application No. PCT/US2008/082598, mailed Feb. 18, 2009, 11 pages.

International Search Report for PCT/US2005/038942, date of mailing Mar. 2, 2006, 3 pages.

International Search Report for PCT/US2005/038943, date of mailing, Mar. 16, 2006, 4 pages.

International Search Report for PCT/US2005/038944, date of mailing, Mar. 31, 2006, 3 pages.

International Search Report for PCT/US2005/038762, date of mailing Oct. 2, 2006, 2 pages.

International Search Report for PCT/US2005/038761, date of mailing Oct. 4, 2006, 2 pages.

International Search Report for PCT/US2005/038970, date of mailing, Oct. 25, 2006, 3 pages.

Non-Final Office Action for U.S. Appl. No. 10/978,680, dated Dec. 26, 2007, 7 pages.

Non-Final Office Action for U.S. Appl. No. 10/978,680, dated Mar. 11, 2008, 15 pages.

Non-Final Office Action for U.S. Appl. No. 10/978,617, dated Apr. 2, 2008, 12 pages.

Non-Final Office Action for U.S. Appl. No. 10/978,617, dated Oct. 10, 2008, 5 pages.

Non-Final Office Action for U.S. Appl. No. 10/978,680, dated Oct. 29, 2008, 14 pages.

Non-Final Office Action for U.S. Appl. No. 10/978,680, dated Apr. 2, 2009, 16 pages.

Non-Final Office Action for U.S. Appl. No. 10/978,680, dated Oct. 13, 2009, 22 pages.

Notice of Allowance and Interview Summary for U.S. Appl. No. 10/978,617, dated Feb. 27, 2009, 7 pages.

Notice of Allowance for U.S. Appl. No. 12/429,061, mail date Mar. 26, 2010, 6 pages.

Office Action for U.S. Appl. No. 12/429,061, mail date Nov. 16, 2009, 5 pages.

Request for Continued Examination and Amendment and Reply for U.S. Appl. No. 10/978,680, filed Sep. 29, 2008, 21 pages.

Request for Continued Examination and Amendment and Reply for U.S. Appl. No. 10/978,680, filed Aug. 12, 2010, 22 pages.

Restriction Response for U.S. Appl. No. 12/429,061, filed Oct. 2, 2009, 8 pages.

Request for Continued Examination (RCE) and Amendment and Reply for U.S. Appl. No. 10/978,680, filed Aug. 12, 2010, 22 pages.

Notice of Allowance for U.S. Appl. No. 10/978,680, dated Sep. 13, 2010, 9 pages.

LITHIUM-ION BATTERY

CROSS-REFERENCE TO RELATED APPLICATIONS

The present application is a Divisional of U.S. patent application Ser. No. 12/429,061 filed Apr. 23, 2009 (now U.S. Pat. No. 7,740,985), which is a Divisional of U.S. patent application Ser. No. 10/978,617 filed Oct. 29, 2004 (now U.S. Pat. No. 7,563,541). The entire disclosures of U.S. patent application Ser. No. 12/429,061 and U.S. patent application Ser. No. 10/978,617 are incorporated herein by reference.

BACKGROUND

The present invention relates generally to the field of lithium batteries. Specifically, the present invention relates to lithium-ion batteries that are relatively tolerant to over-discharge conditions.

Lithium-ion batteries include a positive current collector (e.g., aluminum such as an aluminum foil) having an active material provided thereon (e.g., $LiCoO_2$) and a negative current collector (e.g., copper such as a copper foil) having an active material (e.g., a carbonaceous material such as graphite) provided thereon. Together the positive current collector and the active material provided thereon are referred to as a positive electrode, while the negative current collector and the active material provided thereon are referred to as a negative electrode.

FIG. 1 shows a schematic representation of a portion of a lithium-ion battery 10 such as that described above. The battery 10 includes a positive electrode 20 that includes a positive current collector 22 and a positive active material 24, a negative electrode 30 that includes a negative current collector 32 and a negative active material 34, an electrolyte material 40, and a separator (e.g., a polymeric microporous separator, not shown) provided intermediate or between the positive electrode 20 and the negative electrode 30. The electrodes 20, 30 may be provided as relatively flat or planar plates or may be wrapped or wound in a spiral or other configuration (e.g., an oval configuration). The electrode may also be provided in a folded configuration.

During charging and discharging of the battery 10, lithium ions move between the positive electrode 20 and the negative electrode 30. For example, when the battery 10 is discharged, lithium ions flow from the negative electrode 30 to the to the positive electrode 20. In contrast, when the battery 10 is charged, lithium ions flow from the positive electrode 20 to the negative electrode 30.

FIG. 2 is a graph 100 illustrating the theoretical charging and discharging behavior for a conventional lithium-ion battery. Curve 110 represents the electrode potential versus a lithium reference electrode for a positive electrode that includes an aluminum current collector having a $LiCoO_2$ active material provided thereon, while curve 120 represents the electrode potential versus a lithium reference electrode for a negative electrode that includes a copper current collector having a carbonaceous active material provided thereon. The difference between curves 110 and 120 is representative of the overall cell voltage.

As shown in FIG. 2, upon initial charging to full capacity, the potential of the positive electrode, as shown by curve 110, increases from approximately 3.0 volts to a point above the corrosion potential of copper used to form the negative electrode (designated by dashed line 122). The potential of the negative electrode decreases from approximately 3.0 volts to a point below the decomposition potential of the $LiCoO_2$ active material provided on the aluminum current collector (designated by dashed line 112). Upon initial charging, the battery experiences an irreversible loss of capacity due to the formation of a passive layer on the negative current collector, which may be referred to as a solid-electrolyte interface ("SEI"). The irreversible loss of capacity is shown as a ledge or shelf 124 in curve 120.

One difficulty with conventional lithium-ion batteries is that when such a battery is discharged to a point near zero volts, it may exhibit a loss of deliverable capacity and corrosion of the negative electrode current collector (copper) and possibly of the battery case, depending on the material used and the polarity of the case. As shown in FIG. 2, after initial charging of the battery, a subsequent discharge of the battery in which the voltage of the battery approaches zero volts (i.e., zero percent capacity) results in a negative electrode potential that follows a path designated by dashed line 126. As shown in FIG. 2, the negative electrode potential levels off or plateaus at the copper corrosion potential of the negative current collector (approximately 3.5 volts for copper and designated by dashed line 122 in FIG. 2).

The point at which the curves 110 and 120 cross is sometimes referred to as the zero voltage crossing potential, and corresponds to a cell voltage that is equal to zero (i.e., the difference between the two curves equals zero at this point). Because of the degradation of the copper current collector which occurs at the copper corrosion potential, the copper material used for the negative current collector corrodes before the cell reaches a zero voltage condition, resulting in a battery that exhibits a dramatic loss of deliverable capacity.

While FIG. 2 shows the theoretical charging and discharging behavior of a battery that may experience corrosion of the negative current collector when the battery approaches a zero voltage configuration, it should be noted that there may also be cases in which the active material on the positive current collector may degrade in near-zero-voltage conditions. In such cases, the theoretical potential of the positive electrode versus a lithium reference electrode would decrease to the decomposition potential of the positive active material (shown as line 112 in FIG. 2), at which point the positive active material would decompose, resulting in potentially decreased protection against future over-discharge conditions.

Because damage to the lithium-ion battery may occur in the event of a low voltage condition, conventional lithium-ion batteries may include protection circuitry and/or may be utilized in devices that include protection circuitry which substantially reduces the current drain from the battery (e.g., by disconnecting the battery).

The medical device industry produces a wide variety of electronic and mechanical devices for treating patient medical conditions. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life.

It may be desirable to provide a source of battery power for such medical devices, including implantable medical devices. In such cases, it may be advantageous to provide a battery that may be recharged. It may also be advantageous to provide a battery that may be discharged to a near zero voltage condition without substantial risk that the battery may be damaged (e.g., without corroding one of the electrodes or the battery case, decomposing the positive active material, etc.)

such that the performance of the battery is degraded in subsequent charging and discharging operations.

It would be advantageous to provide a battery (e.g., a lithium-ion battery) that may be discharged to near zero volts without producing a subsequent decrease in the amount of deliverable capacity or producing a corroded negative electrode or battery case. It would also be advantageous to provide a battery that compensates for the irreversible loss of capacity resulting from initial charging of the battery to allow the battery to be used in near zero voltage conditions without significant degradation to battery performance. It would also be advantageous to provide a medical device (e.g., an implantable medical device) that utilizes a battery that includes any one or more of these or other advantageous features.

SUMMARY

An exemplary embodiment relates to a lithium-ion battery that includes a positive electrode comprising a current collector and a first active material and a negative electrode comprising a current collector, a second active material, and a third active material. The second active material comprises a lithium titanate material and the third active material is selected from the group consisting of $Li_xVO_2$ where x is between 0.05 and 0.4, $LiM_xMn_{(2-x)}O_4$ where M is a metal and x is less than or equal to 1, $V_6O_{13}$, $V_2O_5$, $V_3O_8$, $MoO_3$, $TiS_2$, $WO_2$, $MoO_2$, $RuO_2$, and combinations thereof. The third active material exhibits charging and discharging capacity below a corrosion potential of the current collector of the negative electrode and above a decomposition potential of the first active material.

Another exemplary embodiment relates to a battery that includes a positive electrode and a negative electrode. The positive electrode comprises a $LiCoO_2$ active material and the negative electrode comprises a first active material and a second active material. The first active material comprises a lithium titanate material and the second active material exhibits charging and discharging capacity below a corrosion potential of a current collector of the negative electrode and above a decomposition potential of the $LiCoO_2$ active material and comprises at least one material selected from the group consisting of $V_6O_{13}$, $V_2O_5$, $V_3O_8$, $MoO_3$, $TiS_2$, $WO_2$, $MoO_2$, and $RuO_2$.

Another exemplary embodiment relates to a battery that includes a positive electrode and a negative electrode, the positive electrode comprising a first active material selected from the group consisting of $LiCoO_2$ and $LiMn_2O_4$ and the negative electrode comprising a second active material and a third active material. The second active material comprises $Li_4Ti_5O_{12}$ and the third active material comprises at least one material selected from the group consisting of $Li_xVO_2$ where x is less than or equal to 1, $V_6O_{13}$, $V_2O_5$, $V_3O_8$, $MoO_3$, $TiS_2$, $WO_2$, $MoO_2$, and $RuO_2$.

DETAILED DESCRIPTION OF THE EXEMPLARY EMBODIMENTS

Figure 1:
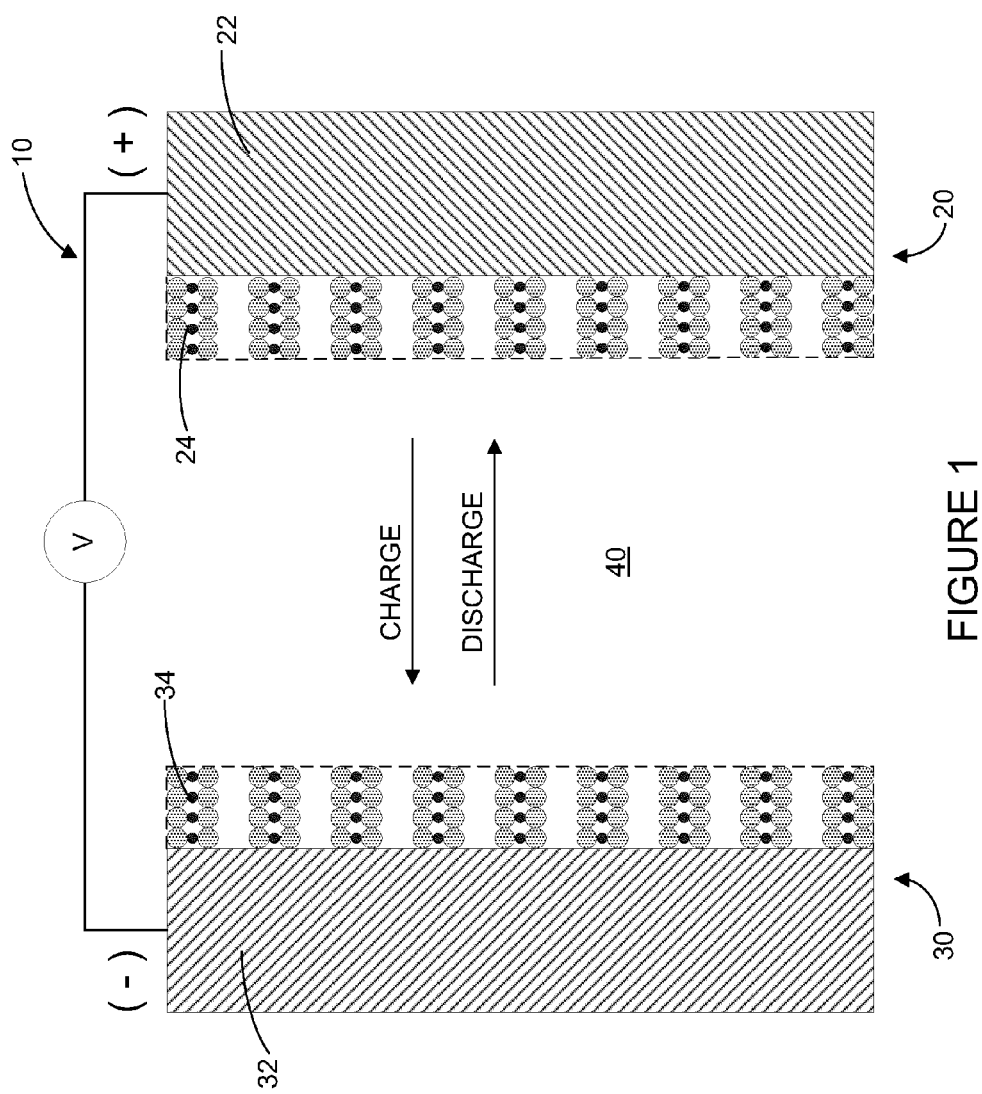
FIG. 1 is a schematic cross-sectional view of a conventional lithium-ion battery.
Figure 2:
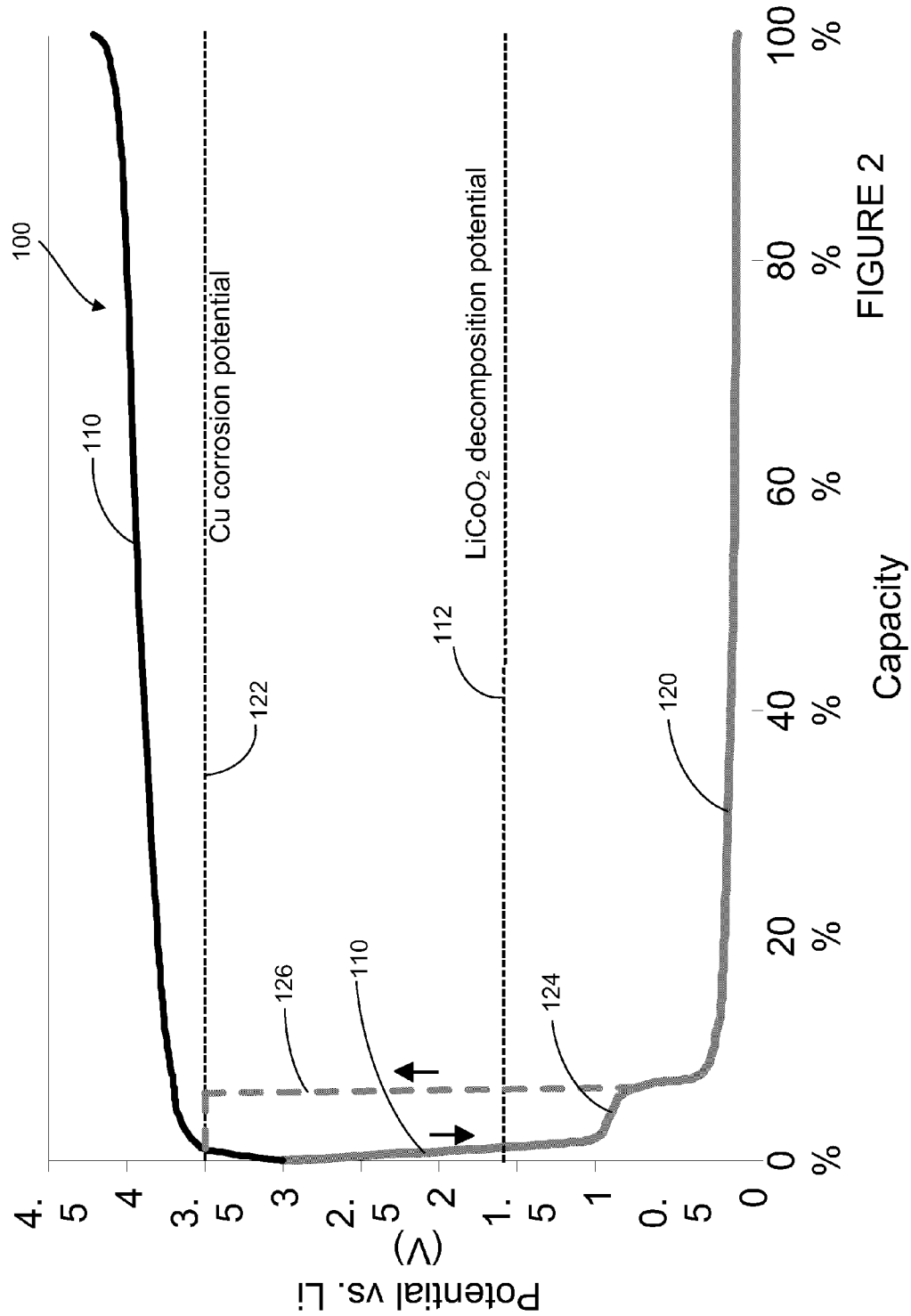
FIG. 2 is a graph illustrating the theoretical charging and discharging behavior for a conventional lithium-ion battery such as that shown schematically in FIG. 1.
Figure 3:
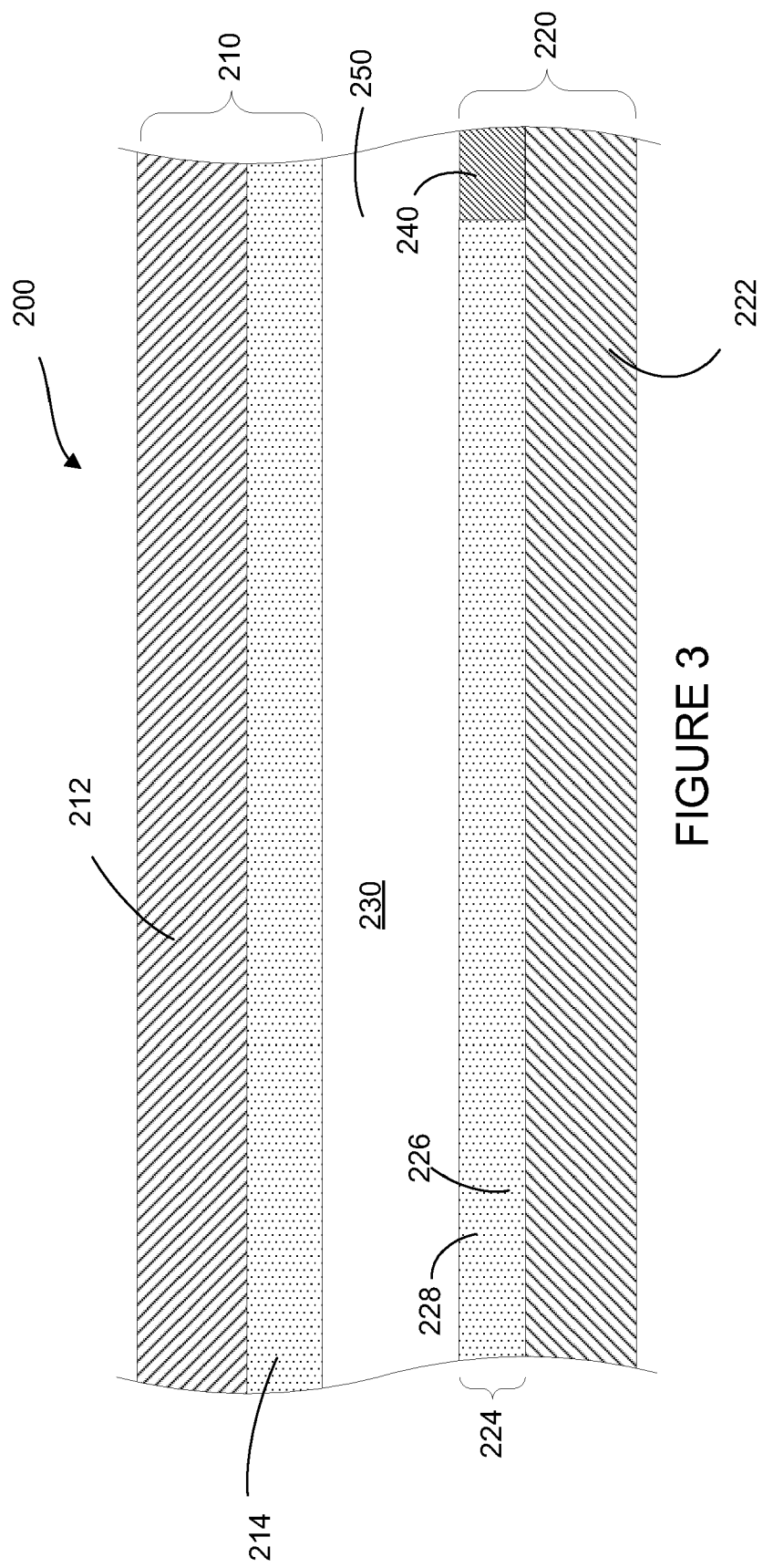
FIG. 3 is a schematic cross-sectional view of a portion of a lithium-ion battery according to an exemplary embodiment.

With reference to FIG. 3, a schematic cross-sectional view of a portion of a lithium-ion battery 200 is shown according to an exemplary embodiment. According to an exemplary embodiment, the battery 200 has a rating of between approximately 10 and 1000 milliampere hours (mAh). According to another exemplary embodiment, the battery has a rating of between approximately 100 and 400 mAh. According to another exemplary embodiment, the battery is an approximately 300 mAh battery. According to another exemplary embodiment, the battery is an approximately 75 mAh battery.

The battery 200 includes at least one positive electrode 210 and at least one negative electrode 220. The electrodes may be provided as flat or planar components of the battery 200, may be wound in a spiral or other configuration, or may be provided in a folded configuration. For example, the electrodes may be wrapped around a relatively rectangular mandrel such that they form an oval wound coil for insertion into a relatively prismatic battery case. According to other exemplary embodiments, the battery may be provided as a button cell battery, a thin film solid state battery, or as another lithium-ion battery configuration.

The battery case (not shown) may be made of stainless steel or another metal. According to an exemplary embodiment, the battery case may be made of titanium, aluminum, or alloys thereof. According to another exemplary embodiment, the battery case may be made of a plastic material or a plastic-foil laminate material (e.g., an aluminum foil provided intermediate a polyolefin layer and a polyester layer).

According to an exemplary embodiment, the negative electrode is coupled to a stainless steel case by a member or tab comprising nickel or a nickel alloy. An aluminum or aluminum alloy member or tab may be coupled or attached to the positive electrode. The nickel and aluminum tabs may serve as terminals for the battery according to an exemplary embodiment.

The dimensions of the battery 200 may differ according to a variety of exemplary embodiments. For example, according to one exemplary embodiment in which the electrodes are wound such that they may be provided in a relatively prismatic battery case, the battery has dimensions of between approximately 30-40 mm by between approximately 20-30 mm by between approximately 5-7 mm. According to another exemplary embodiment, the dimensions of the battery are approximately 20 mm by 20 mm by 3 mm. According to another exemplary embodiment, a battery may be provided in the form of a button cell type battery having a diameter of approximately 30 mm and a thickness of approximately 3 mm. It will be appreciated by those of skill in the art that such dimensions and configurations as are described herein are illustrative only, and that batteries in a wide variety of sizes, shapes, and configurations may be produced in accordance with the novel concepts described herein.

An electrolyte 230 is provided intermediate or between the positive and negative electrodes to provide a medium through which lithium ions may travel. According to an exemplary embodiment, the electrolyte may be a liquid (e.g., a lithium salt dissolved in one or more non-aqueous solvents). According to another exemplary embodiment, the electrolyte may be a lithium salt dissolved in a polymeric material such as poly (ethylene oxide) or silicone. According to another exemplary embodiment, the electrolyte may be an ionic liquid such as N-methyl-N-alkylpyrrolidinium bis(trifluoromethanesulfonyl)imide salts. According to another exemplary embodiment, the electrolyte may be a solid state electrolyte such as a lithium-ion conducting glass such as lithium phosphorous oxynitride (LiPON).

Various other electrolytes may be used according to other exemplary embodiments. For example, according to an exemplary embodiment, the electrolyte may be a 1:1 mixture of ethylene carbonate to diethylene carbonate (EC:DEC) in a 1.0 M salt of $LiPF_6$. According to another exemplary embodiment, the electrolyte may include a polypropylene carbonate solvent and a lithium bis-oxalatoborate salt (sometimes referred to as LiBOB). According to other exemplary embodiments, the electrolyte may comprise one or more of a PVDF copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid or gel, among others.

A separator 250 is provided intermediate or between the positive electrode 210 and the negative electrode 220. According to an exemplary embodiment, the separator 250 is a polymeric material such as a polypropylene/polyethelene or another polyolefin multilayer laminate that includes micropores formed therein to allow electrolyte and lithium ions to flow from one side of the separator to the other. The thickness of the separator 250 is between approximately 10 micrometers (μm) and 50 μm according to an exemplary embodiment. According to a particular exemplary embodiment, the thickness of the separator is approximately 25 μm and the average pore size of the separator is between approximately 0.02 μm and 0.1 μm.

The positive electrode 210 includes a current collector 212 made of a conductive material such as a metal. According to an exemplary embodiment, the current collector 212 comprises aluminum or an aluminum alloy. According to an exemplary embodiment, the thickness of the current collector 212 is between approximately 5 μm and 75 μm. According to a particular exemplary embodiment, the thickness of the current collector 212 is approximately 20 μm. It should also be noted that while the positive current collector 212 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

The current collector 212 has a layer of active material 214 provided thereon (e.g., coated on the current collector). While FIG. 3 shows that the active material 214 is provided on only one side of the current collector 212, it should be understood that a layer of active material similar or identical to that shown as active material 214 may be provided or coated on both sides of the current collector 212.

According to an exemplary embodiment, the active material 214 is a material or compound that includes lithium. The lithium included in the active material 214 may be doped and undoped during discharging and charging of the battery, respectively. According to an exemplary embodiment, the active material 214 is lithium cobalt oxide ($LiCoO_2$). According to another exemplary embodiment, the positive active material is of the form $LiCo_xNi_{(1-x)}O_2$, with x being between approximately 0.05 and 0.8. According to another exemplary embodiment, the primary active material is of the form $LiAl_x Co_yNi_{(1-x-y)}O_2$, where x is between approximately 0.05 and 0.3 and y is between approximately 0.1 and 0.3. According to other exemplary embodiments, the primary active material may include $LiMn_2O_4$.

According to various other exemplary embodiments, the active material provided on the current collector 212 may include a material such as a material of the form $Li_{1-x}MO_2$ where M is a metal (e.g., $LiCoO_2$, $LiNiO_2$, and $LiMnO_2$), a material of the form $Li_{1-w}(M'_xM''_y)O_2$ where M' and M" are different metals (e.g., $Li(Ni_xMn_y)O_2$, $Li(Ni_{1/2}Mn_{1/2})O_2$, $Li(Cr_xMn_{1-x})O_2$, $Li(Al_xMn_{1-x})O_2$, $Li(Co_xM_{1-x})O_2$, $Li(Co_xNi_{1-x})O_2$, and $Li(Co_xFe_{1-x})O_2$)), a material of the form $Li_{1-w}(Mn_xNi_yCo_z)O_2$ (e.g., $LiCo_xMn_yNi_{(1-x-y)}O_2$, $Li(Mn_{1/3}Ni_{1/3}Co_{1/3})O_2$, $Li(Mn_{1/3}Ni_{1/3}Co_{1/3-x}Mg_x)O_2$, $Li(Mn_{0.4}Ni_{0.4}Co_{0.2})O_2$, and $Li(Mn_{0.1}Ni_{01}Co_{0.8})O_2$), a material of the form $Li_{1-w}(Mn_xNi_yCo_{1-2x})O_2$, a material of the form $Li_{1-w}(Mn_xNi_yCo_zAl_w)O_2$, a material of the form $Li_{1-w}(Ni_xCo_yAl_z)O_2$ (e.g., $Li(Ni_{0.8}CO_{0.15}Al_{0.05})O_2$), a material of the form $Li_{1-w}(Ni_xCo_yM_z)O_2$, where M is a metal, a material of the form $Li_{1-w}(Ni_xMn_yM_x)O_2$, where M is a metal, a material of the form $Li(Ni_{x-y}Mn_yCr_{2-x})O_4$, $LiMn_2O_4$, a material of the form $LiM'M''_2O_4$ where M' and M" are different metals (e.g., $LiMn_{2-y-z}Ni_y$, $Li_zO_4$, $LiMn_{1.5}Ni_{0.5}O_4$, $LiNiCuO_4$, $LiMn_{1-x}Al_xO_4$, $LiNi_{0.5}Ti_{0.5}O_4$, and $Li_{1.05}Al_{0.1}Mn_{1.85}O_{4-z}F_z$), $Li_2MnO_3$, a material of the form $Li_xV_yO_z$ (e.g., $LiV_3O_8$, $LiV_2O_5$, and $LiV_6O_{13}$), a material of the form $LiMPO_4$ where M is a metal or $LiM_xM''_{1-x}PO_4$ where M' and M" are different metals (e.g., $LiFePO_4$, $LiFe_xM_{1-x}PO_4$, $LiVOPO_4$, and $Li_3V_2(PO_4)_3$), and $LIMPO_{4x}$ where M is a metal such as iron or vanadium and x is a halogen such as fluorine, and combinations thereof.

A binder material may also be utilized in conjunction with the active material 214. For example, according to an exemplary embodiment, the active material may include a conductive additive such as carbon black and a binder such as polyvinylidine fluoride (PVDF) or an elastomeric polymer.

According to an exemplary embodiment, the thickness of the active material 214 is between approximately 0.1 μm and 3 mm. According to a particular exemplary embodiment, the thickness of the active material 214 is between approximately 25 μm and 300 μm. According to a particular exemplary embodiment, the thickness of the layer of active material 214 is approximately 75 μm.

The negative electrode 220 includes a current collector 222 that is made of a conductive material such as a metal. According to an exemplary embodiment, the current collector 222 is copper or a copper alloy. According to another exemplary embodiment, the current collector 222 may be titanium or a titanium alloy. According to another exemplary embodiment, the current collector 222 is nickel or a nickel alloy. According to another exemplary embodiment in which the negative active material 224 is not carbon, the current collector 222 is aluminum or an aluminum alloy. It should also be noted that while the negative current collector 222 has been illustrated and described as being a thin foil material, the positive current collector may have any of a variety of other configurations according to various exemplary embodiments. For example, the positive current collector may be a grid such as a mesh grid, an expanded metal grid, a photochemically etched grid, or the like.

According to an exemplary embodiment, the thickness of the current collector 222 is between approximately 100 nm and 100 μm. According to a particular exemplary embodiment, the thickness of the current collector 222 is between approximately 5 μm and 25 μm. According to a particular exemplary embodiment, the thickness of the current collector is approximately 10 μm.

The negative current collector 222 has a layer of active material 224 provided thereon. While FIG. 3 shows that the active material 224 is provided on only one side of the current collector 222, it should be understood that a layer of active material similar or identical to that shown may be provided or coated on both sides of the current collector 222.

Layer 224 includes a primary active material 226 and a secondary or auxiliary active material 228. While the primary active material 226 and the secondary active material 228 are shown as being provided as a single layer of material in FIG. 3, it will be appreciated that the primary active material 226 and the secondary active material 228 may be provided as separate individual layers (see, e.g., FIG. 4). A binder material and/or a solvent (not shown) may also be utilized in conjunction with the active material 224. For example, according to an exemplary embodiment, the active material may include a conductive additive such as carbon black and a binder such as polyvinylidine fluoride (PVDF) or an elastomeric polymer.

According to exemplary embodiment, the primary active material 226 is a carbonaceous material (e.g., carbon such as graphite). According to another exemplary embodiment, the primary active material 226 is a lithium titanate material such as $Li_4Ti_5O_{12}$. One advantage of using a lithium titanate material in place of a carbonaceous material is that it is believed that the use of a lithium titanate material allows for charging and discharging of the battery at higher rates than is capable using carbonaceous materials.

Other lithium titanate materials which may be suitable for use as the negative active material may include one or more of include the following lithium titanate spinel materials: $H_xLi_{y-x}TiO_xO_4$, $H_xLi_{y-x}TiO_xO_4$, $Li_4M_xTi_{5-x}O_{12}$, $Li_xTiO_4$, $Li_xTiO_4[Ti_{1.67}Li_{0.33-y}M_y]O_4$, $Li_2TiO_3$, $Li_{4.75}V_{0.25}O_{12}$, $Li_4Ti_{4.75}Fe_{0.25}O_{11.88}$, and $Li_4Ti_{4.5}Mn_{0.5}O_{12}$, and LiM'M"XO_4 (where M' is a metal such as nickel, cobalt, iron, manganese, vanadium, copper, chromium, molybdenum, niobium, or combinations thereof), M" is an optional three valent non-transition metal, and X is zirconium, titanium, or a combination of these two. Note that such lithium titanate spinel materials may be used in any state of lithiation (e.g., $Li_{4+x}Ti_5O_{12}$, where $0 \leq x \leq 3$).

One advantage of using a lithium titanate material instead of a carbonaceous material is that it is believed that the use of a lithium titanate material allows for charging and discharging of the battery at higher rates than is capable using carbonaceous materials. According to other exemplary embodiments, the negative active material 224 may be carbon, $Li_xAl$, $Li_xSn$, $Li_xSi$, $Li_xSnO$, metal nanoparticle composites (e.g., including $Li_xAl$, $Li_xSn$, $Li_xSi$, or $Li_xSnO$), or carbon-coated lithium titanate. Lithium titanate materials are also believed to offer superior cycle life because they are so called "zero-strain" materials. Zero strain materials have crystal lattices which do not experience shrinkage or contraction with lithium doping/de-doping, making them free from strain-related degradation mechanisms.

Another advantageous feature of using a lithium titanate material is that it is believed that when used in a negative electrode of a lithium-ion battery, such materials will cycle lithium at a potential plateau of about 1.5 V versus a lithium reference electrode. This is substantially higher than graphitic carbon, which is traditionally used in lithium ion batteries, and cycles lithium down to about 0.1 V in the fully charged state. As a result, the battery using lithium titanate is believed to be less likely to result in plating of lithium (which occurs at 0 V versus a lithium reference) while being charged. Lithium plating is a well-known phenomenon that can lead to loss in performance of lithium ion batteries. Being free from the risk lithium plating, cells with lithium titanate negative electrodes may also be charged at rates that exceed those with carbon negative electrodes. For example, a common upper limit for the rate of charge in lithium ion batteries is about 1C (meaning that the battery can be fully charged from the discharged state in one hour). Conversely, it has been reported in literature that lithium titanate may be charged at rates up to 10C (i.e., attaining full charge in 1/10 hour, or six minutes). Being able to recharge a battery more quickly substantially increases the functionality of devices that employ such a battery. A further advantage of the higher potential of the lithium titanate material is that it avoids decomposition of organic solvents (such as propylene carbonate) commonly used in lithium ion batteries. In so doing, it may reduce negative consequences such as formation of gas, cell swelling, and reduction of reversible battery capacity.

The secondary active material 228 is a material that is selected to have relatively significant charge and discharge capacity below the corrosion potential of the material used for a negative current collector 222 provided as part of the negative electrode 220 and above the decomposition potential of the active material 214 provided on the positive current collector 212. The secondary active material is also selected to be stable over its full potential-composition range in the electrolyte. For example, according to an exemplary embodiment in which the negative current collector 222 comprises copper, for which the corrosion potential is approximately 3.5 volts, the secondary active material 228 includes significant charge and discharge capacity below 3.5 volts.

The secondary active material 228 may or may not contain lithium. According to an exemplary embodiment in which the secondary active material does not include lithium, the secondary active material is $V_6O_{13}$. According to another exemplary embodiment in which the secondary active material includes lithium, the secondary active material is $LiMn_2O_4$. According to various other exemplary embodiments, the secondary active material may be selected from the following materials and combinations thereof: $V_2O_5$, $V_6O_{13}$, $LiMn_2O_4$ (spinel), $LiM_xMn_{(2-x)}O_4$ (spinel) where M is metal (including Li) and x is between approximately 0.05 and 0.4, $Li_4Ti_5O_{12}$, $Li_xVO_2$ (where x is between approximately 0 and 1), $V_3O_8$, $MoO_3$, $TiS_2$, $WO_2$, $MoO_2$, and $RuO_2$, as well as their partially or fully lithiated counterparts.

Any lithium included in the secondary active material 228 of the negative electrode has significant charge/discharge capacity that lies below the corrosion potential of the negative current collector and/or any battery components to which it is electrically connected (e.g., the case) and above the decomposition potential of the positive electrode active material. The secondary active material contains electrochemically active lithium in the as-constructed state. The lithium becomes significantly doped at a potential below the corrosion potential for the negative current collector 222. In so doing, this material lowers the final potential of the positive electrode in the discharge state, so that the zero voltage crossing potential remains below the corrosion potential of the negative current collector and the battery case. The secondary active material may be capable of releasing the lithium when the battery is charged.

It should be noted that while a variety of materials have been described above as being useful for secondary active material 228, a variety of additional materials may be utilized in addition to or in place of such materials. For example, the secondary active material may comprise an oxide material such as one or more of $Li_xMoO_3$ ($0<x\leq2$), $Li_xMoO_2$ ($0<x\leq1$), $Li_xMo_2O_4$ ($0<x\leq2$), $Li_xMnO_2$ ($0<x\leq1$), $Li_xMn_2O_4$ ($0<x\leq2$), $Li_xV_2O_5$ ($0<x\leq2.5$), $Li_xV_3O_8$ ($0<x\leq3.5$), $Li_xV_6O_{13}$ ($0<x\leq6$ for $Li_xVO_{2.19}$ and $0<x\leq3.6$ for $Li_xVO_{2.17}$), $Li_xVO_2$ ($0<x\leq1$), $Li_xWO_3$ ($0<x\leq1$), $Li_xWO_2$ ($0<x\leq1$), $Li_xTiO_2$ (anatase) ($0<x\leq1$), $Li_xTi_2O_4$ ($0<x\leq2$), $Li_xRuO_2$ ($0<x\leq1$), $Li_xFe_2O_3$ ($0<x\leq2$), $Li_xFe_3O_4$ ($0<x\leq2$), $Li_xCr_2O$ ($0<x\leq3$), $Li_xCr$ ($0<x\leq3.8$), $Li_xNi_yCo_{1-y}O_2$ ($0<x\leq1$, $0.90<y\leq1.00$), where x is selected such that these materials have little or no lithium that becomes undoped below the corrosion potential of the negative current collector during the first charge of the battery.

According to another exemplary embodiment, the secondary active material may comprise a sulfide material such as one or more of $Li_xV_2S_5$ ($0<x\leq4.8$), $Li_xTaS_2$ ($0<x\leq1$), $Li_xFeS$ ($0<x\leq1$), $Li_xFeS_2$ ($0<x\leq1$), $Li_xNbS_3$ ($0<x\leq2.4$), $Li_xMoS_3$ ($0<x\leq3$), $Li_xMoS_2$ ($0<x\leq1$), $Li_xTiS_2$ ($0<x\leq1$), $Li_xZrS_2$ ($0<x\leq1$), $Li_xFe_{0.25}V_{0.75}S_2$ ($0<x\leq1$), $Li_xCr_{0.75}V_{0.25}S_2$ ($0<x\leq0.65$), $Li_xCr_{0.5}V_{0.5}S_2$ ($0<x\leq1$) where x is selected such that these materials have little or no lithium that becomes undoped below the corrosion potential of the negative current collector during the first charge of the battery.

According to another exemplary embodiment, the secondary active material may comprise a selenide material such as one or more of $Li_xNbSe_3$ ($0<x\leq3$), $Li_xVSe_2$ ($0<x\leq1$). Various other materials may also be used, for example, $Li_xNiPS_3$ ($0<x\leq1.5$) and $Li_xFePS_3$ ($0<x\leq1.5$) where x is selected such that these materials have little or no lithium that becomes undoped below the corrosion potential of the negative current collector during the first charge of the battery.

According to an exemplary embodiment in which the secondary active material 228 does not include lithium in the as-constructed state (e.g., the secondary active material is $V_6O_{13}$), a mechanism is provided to lithiate the secondary active material 228. According to an exemplary embodiment, a mass or quantity of lithium (e.g., a lithium "patch") may be provided, as will be discussed in greater detail below.

According to various exemplary embodiments, the thickness of the active material 224 is between approximately 0.1 µm and 3 mm. According to other exemplary embodiments, the thickness of the layer of active material 224 may be between approximately 25 µm and 300 µm. According to a particular exemplary embodiment, the thickness of the active material 224 is approximately 75 µm. In embodiments in which the primary active material 226 and the secondary active material 228 are provided as separate layers of active material, the thickness of the primary active material 226 is between approximately 25 µm and 300 µm (and approximately 75 µm according to a particular exemplary embodiment), while the thickness of the secondary active material 218 is between approximately 5 µm and 60 µm (and approximately 10 µm according to a particular exemplary embodiment).

Figure 4:
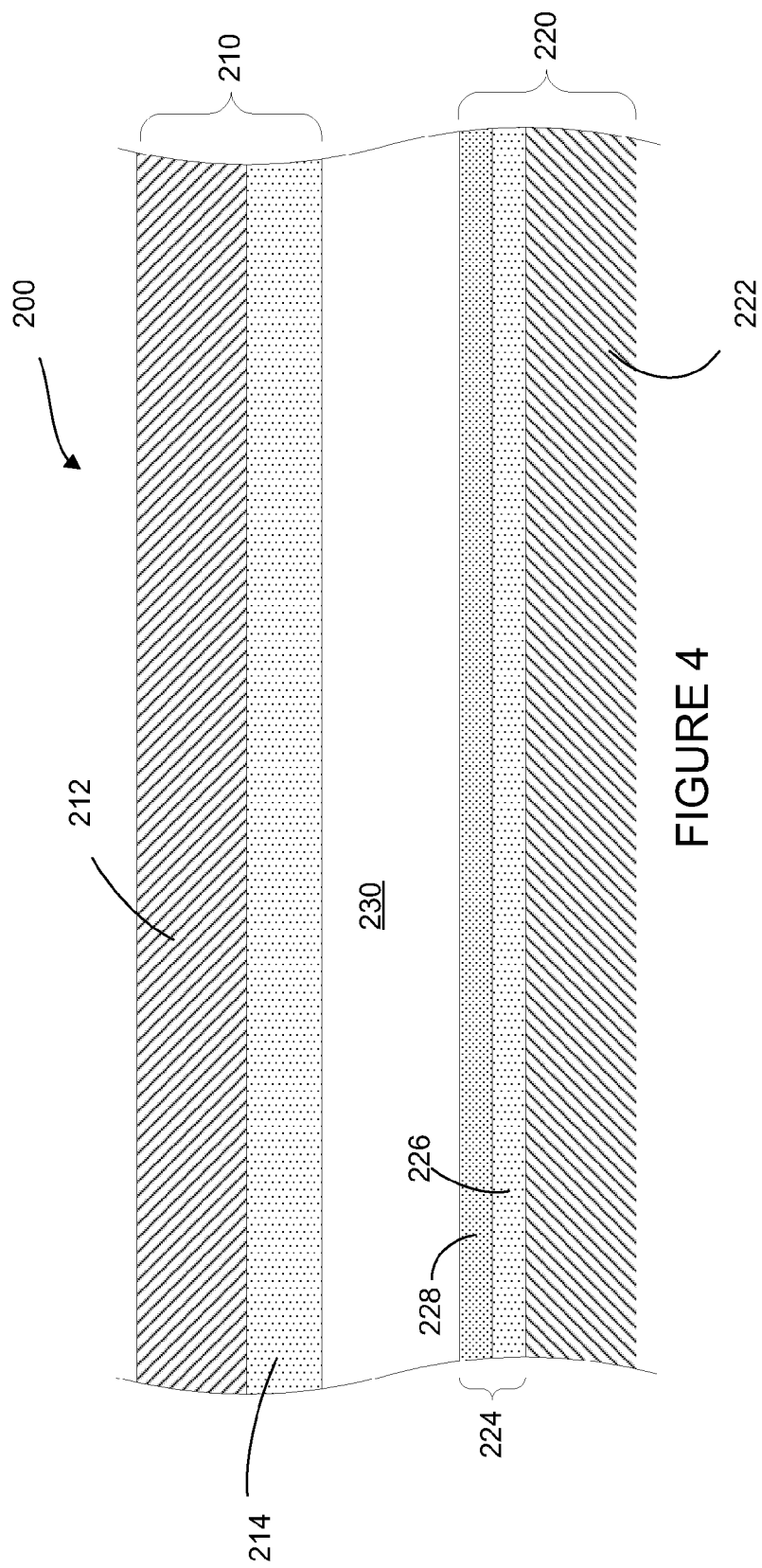
FIG. 4 is a schematic cross-sectional view of a portion of a lithium-ion battery according to another exemplary embodiment.

As shown in FIG. 3, a mass or quantity of electrochemically active lithium (shown as a piece of lithium in the form of a lithium patch or member 240) is shown as being coupled or attached to the negative current collector 222. Such a configuration corresponds to a situation in which the secondary active material 228 is provided without including electrochemically active lithium (e.g., the secondary active material 228 does not include lithium as it is coated on the negative current collector). One such exemplary embodiment involves the use of $V_6O_{13}$ for the secondary active material. In contrast, FIG. 4 shows a configuration in which the secondary active material 228 is provided as a lithiated material (e.g., $LiMn_2O_4$). In such an embodiment, a lithium patch is not necessary.

The electrochemically active lithium may be provided in other locations in the negative electrode 220 and/or may have a different size or shape than that shown schematically in FIG. 3. For example, the electrochemically active lithium may be provided as a disc or as a rectangular piece of material coupled to the negative current collector. While the electrochemically active lithium is shown as being provided on a single side of the current collector 222 in FIG. 3 (e.g., as a lithium patch), separate lithium patches may be provided on opposite sides of the current collector 222. Further, multiple lithium patches may be provided on one or more of the sides of the current collector 222. In another example, the lithium may be provided elsewhere within the battery and connected (e.g., by a wire) to the current collector 222.

The electrochemically active lithium may be added through a chemical or electrochemical process. Such processes could include the addition of butyl lithium or electrical contact with metallic lithium or any other lithium source containing lithium and having an electrochemical potential lower than that of the secondary material (and optionally adding an electrolyte to activate the process). According to another exemplary embodiment, the process may be an electrolytic process, in which the precursor secondary material is polarized to a cathodic potential at which lithium ions present in an electrolyte are inserted into the precursor material. It should also be noted that electrochemically cyclable lithium may be added by adding lithium-containing compounds such as a lithium intermetallic compound such as a lithium-aluminum compound, a lithium-tin compound, a lithium-silicon compound, or any other similar compound that irreversibly donates lithium at a potential below that of the corrosion potential of the negative current collector (and any material to which it is electrically connected).

According to another exemplary embodiment, the electrochemically active or cyclable lithium may be added as finely divided or powdered lithium. Such powdered lithium may include a passive coating (e.g., a thin layer or film of lithium carbonate) provided thereon to reduce the reactivity of the powdered lithium with air and moisture. Such material may be mixed with the negative electrode active material prior to application of the negative electrode active material to fabrication of the cells or may be added as another separate active material layer. According to an exemplary embodiment, the finely divided or powdered lithium particles have a diameter of between approximately 1 µm and 100 µm, and according to a particular embodiment, between approximately 5 µm and 30 µm.

One advantage of providing electrochemically active lithium at the negative electrode (e.g., in the form of one or more lithium patches) is that the secondary active material 228 may be partially or completely lithiated by the lithium to compensate for the irreversible loss of capacity which occurs upon the first charging of the battery 200. For example, when the battery cell is filled with electrolyte, lithium from the lithium patch 240 is oxidized and inserted into the negative active material (i.e., the lithium in the electrochemically active lithium is effectively "shorted" to the negative active material).

The electrochemically active lithium may also provide a number of additional advantages. For example, it may act to maintain the potential of the negative current collector below its corrosion potential prior to initial charging ("formation")

of the battery. The electrochemically active lithium may also aid in the formation of the solid-electrolyte interface ("SEI") at the negative electrode. Further, the electrochemically active lithium may provide the "formation" of the active material on the negative electrode without a corresponding reduction in battery capacity as would occur when the source of lithium for formation is the active material from the positive electrode.

The amount of electrochemically active lithium is selected such the amount of electrochemical equivalents provided by the electrochemically active lithium at minimum corresponds to the irreversible capacity of the negative electrode active material and at maximum corresponds to the sum of the irreversible capacity of the negative electrode active material and the capacity of the secondary active material 228. In this manner, the electrochemically active lithium at least compensates for the irreversible loss of capacity which occurs on initial charging of the battery 200 and most preferably corresponds to the sum of the irreversible capacity of the negative electrode active material and the capacity of the secondary active material 228.

According to an exemplary embodiment in which a lithium patch 240 is utilized, the size of the lithium patch 240 is between approximately 1.4 cm×1.4 cm×0.11 cm, which corresponds to approximately 0.013 grams (e.g., approximately 50 mAh). The specific size of the lithium patch may vary according to other exemplary embodiments (e.g., approximately 5-25 percent of the capacity of either the negative or positive electrode).

Figure 5:
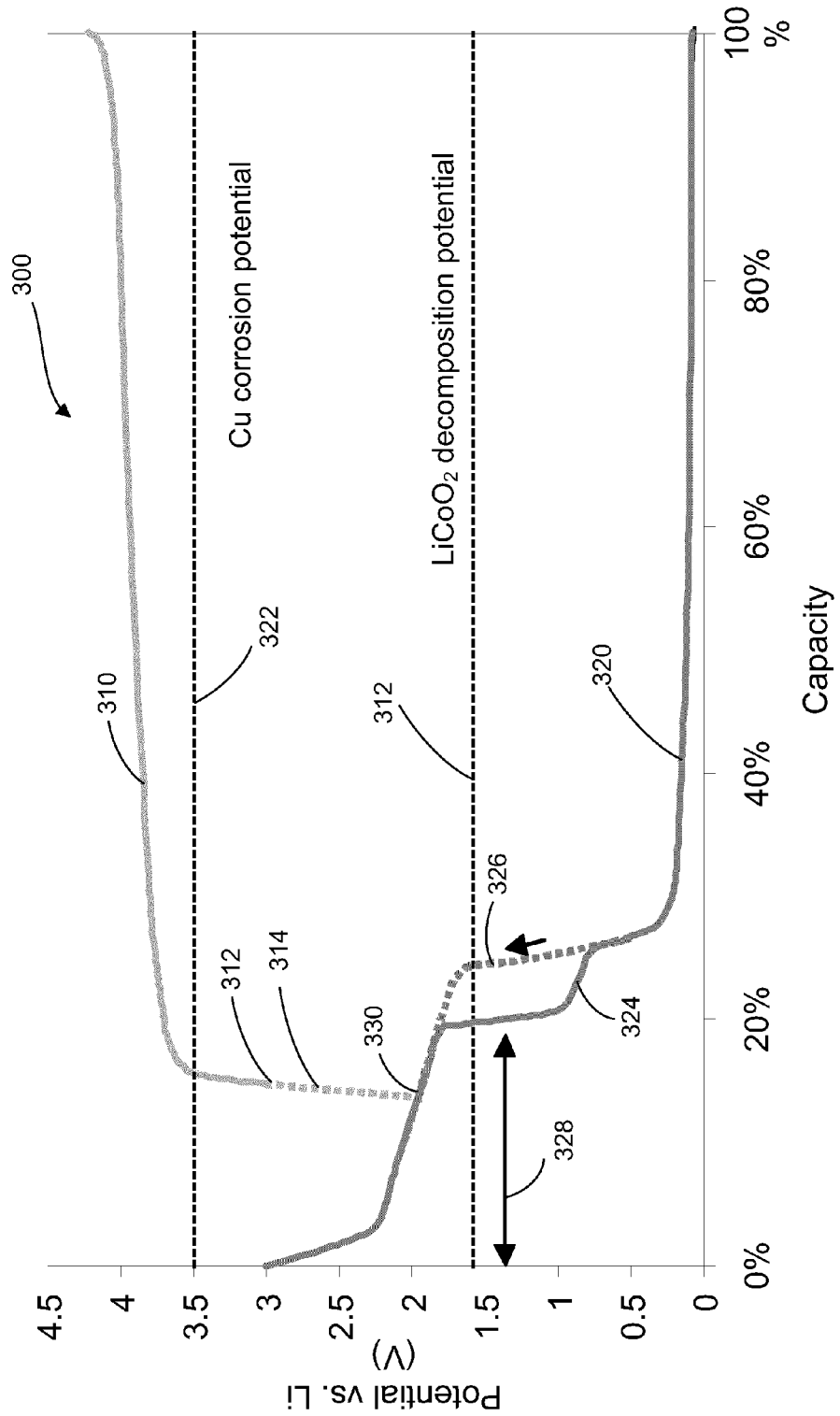
FIG. 5 is a graph illustrating the theoretical charging and discharging behavior for a lithium-ion battery such as that shown in FIG. 3.

FIG. 5 is a graph 300 illustrating the theoretical charging and discharging behavior for a lithium-ion battery constructed in accordance with an exemplary embodiment such as that shown and described with regard to FIG. 3. Curve 310 represents the electrode potential versus a lithium reference electrode for a positive electrode (e.g., positive electrode 210) that includes an aluminum current collector having a $LiCoO_2$ primary active material provided thereon.

Curve 320 represents the electrode potential versus a lithium reference electrode for a negative electrode that includes a copper current collector having a primary active material (i.e., a carbonaceous material such as carbon), a non-lithiated secondary active material, and a lithium patch provided thereon. The difference between curves 310 and 320 is representative of the overall cell voltage of the battery.

The secondary active material is selected to provide significant charging/discharging capacity below the corrosion potential (shown as dashed line 322) of the negative current collector and above the decomposition potential (shown as dashed line 312) of the $LiCoO_2$ positive electrode active material, in addition to its ability to remain stable over its full potential-composition range in the electrolyte. According to an exemplary embodiment, the secondary active material is $V_6O_{13}$. According to various other exemplary embodiments, the secondary active material may be selected from the following materials and combinations thereof: $V_2O_5$, $V_6O_{13}$, $V_3O_8$, $MoO_3$, $TiS_2$, $WO_2$, $MoO_2$, and $RuO_2$.

It should be noted that the theoretical charging and discharge behavior for the negative electrode is believed to be qualitatively similar to that shown in FIG. 5 for a copper current collector having a $Li_4Ti_5O_{12}$ primary active material provided thereon (as opposed to a carbon active material), with the relatively flat portion of the curve 320 being shifted upward to a level of approximately 1.57 volts (in contrast to the approximately 0.1 volts for the carbon active material).

As shown in FIG. 5, upon initial charging to full capacity, the potential of the positive electrode, as shown by curve 310, increases from approximately 3.0 volts (shown as point 311) to a point above the corrosion potential of copper used to form the negative current collector (designated by dashed line 322). When the battery is subsequently discharged toward a zero voltage condition, the positive electrode potential will continue along a portion 314 of curve 310 to a point below approximately 3.0 volts (as shown by the dashed portion of curve 310 in FIG. 5).

The potential of the negative electrode decreases from approximately 3.0 volts on initial charging to a point below the decomposition potential of the $LiCoO_2$ active material provided on the positive current collector (designated by dashed line 312). According to an exemplary embodiment, the corrosion potential of copper is approximately 3.5 volts, while the decomposition potential of the $LiCoO_2$ active material provided on the positive current collector is approximately 1.6 volts. According to another exemplary embodiment, the decomposition potential of the $LiCoO_2$ active material is approximately 1.35 volts.

The initial capacity of the negative electrode is provided by the secondary active material (e.g., $V_6O_{13}$), as illustrated by the portion of the graph 300 designated by arrow 328. After the capacity of the secondary active material is exhausted, the battery experiences an irreversible loss of capacity due to the formation of a passive layer on the negative electrode, which may be referred to as a solid-electrolyte interface ("SEI"). The irreversible loss of capacity is shown as a ledge or shelf 324 in curve 320. The lithium patch is provided so as to compensate for the irreversible loss of capacity, and may be provided such that it compensates both for the initial capacity of the secondary active material (e.g., arrow 328) and the irreversible loss of capacity (ledge 324).

Upon discharging the battery to a point approaching zero volts, the negative electrode potential follows a path designated by a dashed portion 326 of the curve 320. However, because the secondary active material is chosen to have significant charging/discharging capacity below the corrosion potential of the negative current collector and above the decomposition potential of the $LiCoO_2$ primary active material, the zero voltage crossing potential (shown as point 330) is below the corrosion potential of the negative current collector and above the decomposition potential of the $LiCoO_2$ primary active material, thus avoiding corrosion of the negative current collector (and potentially of the battery case or any other battery component in electrical contact or communication with the negative electrode) and any associated loss of battery charging capacity. One advantageous feature of such an arrangement is that the battery may be repeatedly cycled (i.e., charged and discharged) to near-zero-voltage conditions without significant decline in battery performance.

It is intended that a lithium-ion battery such as that described herein may be fully discharged while the materials for both electrodes, including their corresponding current collectors, are stable (e.g., corrosion of the current collectors and/or the decomposition of active material may be avoided, etc.). One potential advantageous feature of such an arrangement is that the occurrence of reduced device functionality (i.e., the need to recharge more frequently) and corrosion of the current collectors and battery case (with the incumbent possibility of leaking potentially corrosive and toxic battery contents) may be reduced or avoided.

Various advantageous features may be obtained by utilizing batteries such as those shown and described herein. For example, use of such batteries may eliminate the need to utilize circuitry to disconnect batteries approaching near-zero voltage conditions. By not utilizing circuitry for this function, volume and cost reductions may be obtained.

According to an exemplary embodiment, lithium-ion batteries such as those described above may be used in conjunction with medical devices such as medical devices that may be implanted in the human body (referred to as "implantable medical devices" or "IMD's").

Figures 6, 7:
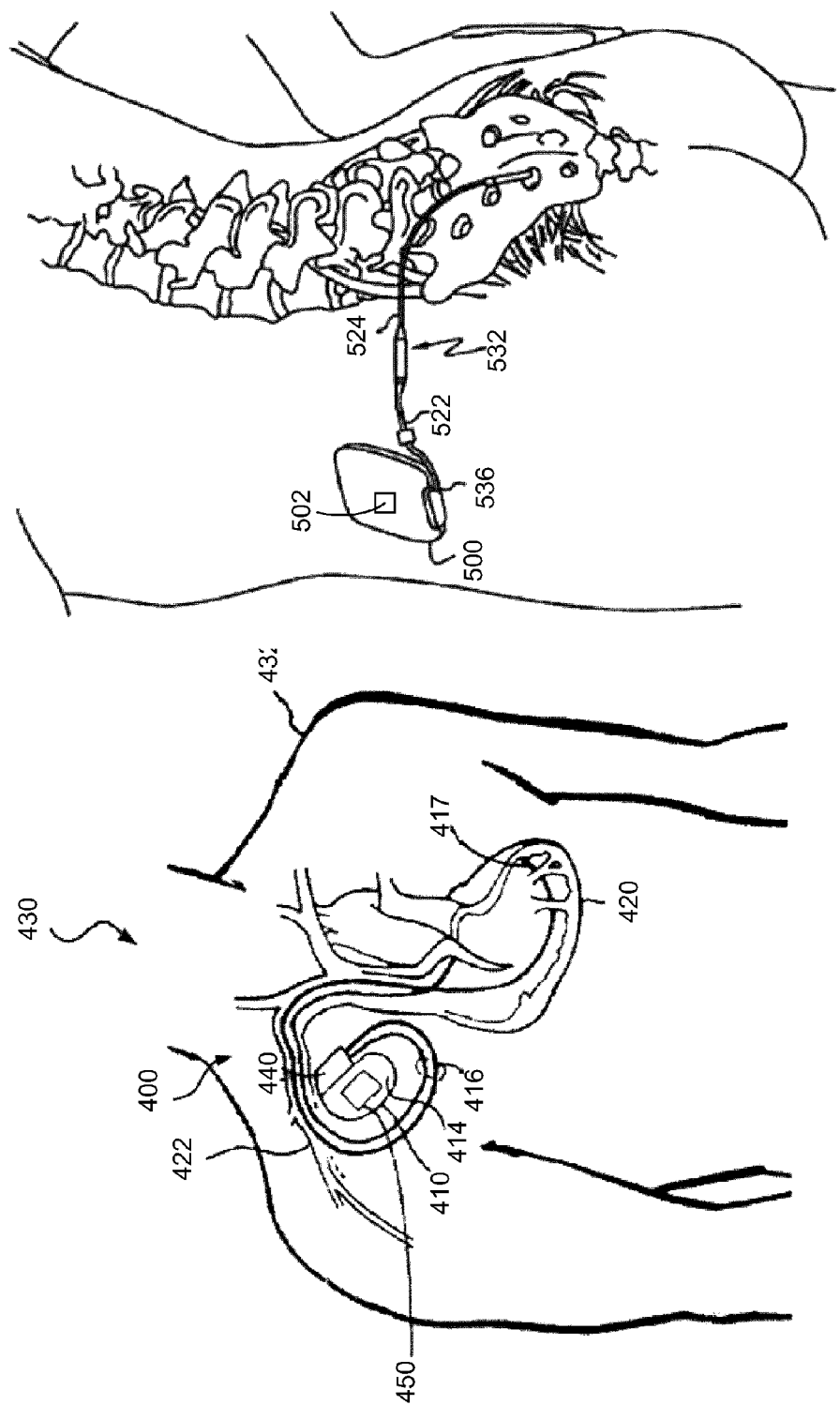
FIG. 6 is a schematic view of a system in the form of an implantable medical device implanted within a body or torso of a patient.
FIG. 7 is schematic view of another system in the form of an implantable medical device.

FIG. 6 illustrates a schematic view of a system 400 (e.g., an implantable medical device) implanted within a body or torso 432 of a patient 430. The system 400 includes a device 410 in the form of an implantable medical device that for purposes of illustration is shown as a defibrillator configured to provide a therapeutic high voltage (e.g., 700 volt) treatment for the patient 430.

The device 410 includes a container or housing 414 that is hermetically sealed and biologically inert according to an exemplary embodiment. The container may be made of a conductive material. One or more leads 416 electrically connect the device 410 and to the patient's heart 420 via a vein 422. Electrodes 417 are provided to sense cardiac activity and/or provide an electrical potential to the heart 420. At least a portion of the leads 416 (e.g., an end portion of the leads shown as exposed electrodes 417) may be provided adjacent or in contact with one or more of a ventricle and an atrium of the heart 420.

The device 410 includes a battery 440 provided therein to provide power for the device 410. According to another exemplary embodiment, the battery 440 may be provided external to the device or external to the patient 430 (e.g., to allow for removal and replacement and/or charging of the battery). The size and capacity of the battery 440 may be chosen based on a number of factors, including the amount of charge required for a given patient's physical or medical characteristics, the size or configuration of the device, and any of a variety of other factors. According to an exemplary embodiment, the battery is a 500 mAh battery. According to another exemplary embodiment, the battery is a 300 mAh battery. According to various other exemplary embodiments, the battery may have a capacity of between approximately 10 and 1000 mAh.

According to other exemplary embodiments, more than one battery may be provided to power the device 410. In such exemplary embodiments, the batteries may have the same capacity or one or more of the batteries may have a higher or lower capacity than the other battery or batteries. For example, according to an exemplary embodiment, one of the batteries may have a capacity of approximately 500 mAh while another of the batteries may have a capacity of approximately 75 mAh.

One or more capacitors (shown as capacitor bank 450) are provided in the device to store energy provided by the battery 440. For example, the system 410 may be configured such that when the device 410 determines that a therapeutic high-voltage treatment is required to establish a normal sinus rhythm for the heart 420, the capacitors in the capacitor bank 450 are charged to a predetermined charge level by the battery 440. Charge stored in the capacitors may then be discharged via the leads 416 to the heart 420. According to another exemplary embodiment, the capacitors may be charged prior to determination that a stimulating charge is required by the heart such that the capacitors may be discharged as needed.

According to another exemplary embodiment shown in FIG. 7, an implantable neurological stimulation device 500 (an implantable neuro stimulator or INS) may include a battery 502 such as those described above with respect to the various exemplary embodiments. Examples of other neuro stimulation products and related components are shown and described in a brochure titled "Implantable Neurostimulation Systems" available from Medtronic, Inc.

An INS generates one or more electrical stimulation signals that are used to influence the human nervous system or organs. Electrical contacts carried on the distal end of a lead are placed at the desired stimulation site such as the spine or brain and the proximal end of the lead is connected to the INS. The INS is then surgically implanted into an individual such as into a subcutaneous pocket in the abdomen, pectoral region, or upper buttocks area. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea. Additional therapies appear promising to treat a variety of physiological, psychological, and emotional conditions. Before an INS is implanted to deliver a therapy, an external screener that replicates some or all of the INS functions is typically connected to the patient to evaluate the efficacy of the proposed therapy.

The INS 500 includes a lead extension 522 and a stimulation lead 524. The stimulation lead 524 is one or more insulated electrical conductors with a connector 532 on the proximal end and electrical contacts (not shown) on the distal end. Some stimulation leads are designed to be inserted into a patient percutaneously, such as the Model 3487A Pisces-Quad® lead available from Medtronic, Inc. of Minneapolis Minn., and stimulation some leads are designed to be surgically implanted, such as the Model 3998 Specify® lead also available from Medtronic.

Although the lead connector 532 can be connected directly to the INS 500 (e.g., at a point 536), typically the lead connector 532 is connected to a lead extension 522. The lead extension 522, such as a Model 7495 available from Medtronic, is then connected to the INS 500.

Implantation of an INS 520 typically begins with implantation of at least one stimulation lead 524, usually while the patient is under a local anesthetic. The stimulation lead 524 can either be percutaneously or surgically implanted. Once the stimulation lead 524 has been implanted and positioned, the stimulation lead's 524 distal end is typically anchored into position to minimize movement of the stimulation lead 524 after implantation. The stimulation lead's 524 proximal end can be configured to connect to a lead extension 522.

The INS 500 is programmed with a therapy and the therapy is often modified to optimize the therapy for the patient (i.e., the INS may be programmed with a plurality of programs or therapies such that an appropriate therapy may be administered in a given situation). In the event that the battery 502 requires recharging, an external lead (not shown) may be used to electrically couple the battery to a charging device or apparatus.

A physician programmer and a patient programmer (not shown) may also be provided to allow a physician or a patient to control the administration of various therapies. A physician programmer, also known as a console programmer, uses telemetry to communicate with the implanted INS 500, so a clinician can program and manage a patient's therapy stored in the INS 500, troubleshoot the patient's INS 500 system, and/or collect data. An example of a physician programmer is a Model 7432 Console Programmer available from Medtronic. A patient programmer also uses telemetry to communicate with the INS 500, so the patient can manage some aspects of her therapy as defined by the clinician. An example of a patient programmer is a Model 7434 Itrel® 3 EZ Patient Programmer available from Medtronic.

While the medical devices described herein (e.g., systems 400 and 500) are shown and described as a defibrillator and a neurological stimulation device, it should be appreciated that other types of implantable medical devices may be utilized according to other exemplary embodiments, such as pacemakers, cardioverters, cardiac contractility modulators, drug administering devices, diagnostic recorders, cochlear implants, and the like for alleviating the adverse effects of various health ailments. According to still other embodiments, non-implantable medical devices or other types of devices may utilize batteries as are shown and described in this disclosure.

It is also contemplated that the medical devices described herein may be charged or recharged when the medical device is implanted within a patient. That is, according to an exemplary embodiment, there is no need to disconnect or remove the medical device from the patient in order to charge or recharge the medical device. For example, transcutaneous energy transfer (TET) may be used, in which magnetic induction is used to deliver energy from outside the body to the implanted battery, without the need to make direct physical contact to the implanted battery, and without the need for any portion of the implant to protrude from the patient's skin. According to an exemplary embodiment, a connector may be provided external to the patient's body that may be electrically coupled to a charging device in order to charge or recharge the battery. According to other exemplary embodiments, medical devices may be provided that may require removal or detachment from the patient in order to charge or recharge the battery.

It should be understood that while the present disclosure describes the use of lithium-ion batteries with a variety of medical devices, such batteries may be used in a variety of other applications, including computers (e.g., laptop computers), phones (e.g., cellular, mobile, or cordless phones), automobiles, and any other device or application for which it may be advantageous to provide power in the form of a lithium-ion battery.

It is also important to note that the construction and arrangement of the lithium-ion battery as shown and described with respect to the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. Accordingly, all such modifications are intended to be included within the scope of the present invention as defined in the appended claims. Other substitutions, modifications, changes and omissions may be made in the design, operating conditions and arrangement of the preferred and other exemplary embodiments without departing from the scope of the present invention as expressed in the appended claims.

What is claimed is:

1. A lithium-ion battery comprising:
a positive electrode comprising a current collector and a first active material, the first active material comprising $LiCoO_2$; and
a negative electrode comprising a current collector, a second active material, and a third active material, wherein the second active material comprises a lithium titanate material and the third active material is $V_2O_5$;
wherein the third active material exhibits charging and discharging capacity below a corrosion potential of the current collector of the negative electrode and above a decomposition potential of the first active material.

2. The lithium-ion battery of claim 1, wherein each of the positive electrode and the negative electrode have a zero voltage crossing potential below the corrosion potential of the current collector of the negative electrode and above the decomposition potential of the first active material.

3. The lithium-ion battery of claim 1, wherein the first active material further comprises a binder material.

4. The lithium-ion battery of claim 1, wherein the current collector of the negative electrode comprises a material selected from the group consisting of copper, nickel, aluminum, and titanium.

5. The lithium-ion battery of claim 4, wherein the second active material comprises $Li_4Ti_5O_{12}$.

6. The lithium-ion battery of claim 1, further comprising a quantity of lithium provided in electrical contact with the current collector of the negative electrode.

7. The lithium-ion battery of claim 6, wherein the quantity of lithium is configured to provide a lithium capacity for the negative electrode sufficient to at least compensate for irreversible loss of capacity of the negative electrode.

8. The lithium-ion battery of claim 6, wherein the quantity of lithium is configured to provide a lithium capacity equal to the sum of the irreversible loss of capacity of the negative electrode and the capacity of the third active material.

9. The lithium-ion battery of claim 1, further comprising a porous polymeric separator provided intermediate the positive electrode and the negative electrode.

10. The lithium-ion battery of claim 9, wherein the porous polymeric separator comprises micropores configured to allow electrolyte to flow from one side of the separator to the other.

11. The lithium-ion battery of claim 1, wherein the first active material is coated on both sides of the positive electrode.

12. The lithium-ion battery of claim 1, wherein the positive electrode and the negative electrode are wound electrodes.

13. The lithium-ion battery of claim 1, further comprising a battery case formed of a stainless steel.

14. The lithium-ion battery of claim 1, further comprising a liquid electrolyte.

15. The lithium-ion battery of claim 14, wherein the liquid electrolyte comprises at least one lithium salt dissolved in at least one non-aqueous solvent.

16. A battery comprising:
a positive electrode and a negative electrode, wherein the positive electrode comprises a first active material comprising $LiCoO_2$ and the negative electrode comprises a second active material comprising a lithium titanate material and a third active material comprising $V_2O_5$.

17. The battery of claim 16, wherein the positive electrode and the negative electrode have zero voltage crossing potentials above the decomposition potential of the first active material and below a corrosion potential of a current collector of the negative electrode.

18. The battery of claim 16, wherein the first active material further comprises a PVDF binder.

19. The battery of claim 16, further comprising a polymeric separator provided intermediate the positive electrode and the negative electrode.

20. The battery of claim 19, wherein the polymeric separator comprises micropores configured to allow electrolyte to flow from one side of the separator to the other.

21. The battery of claim 19, wherein the polymeric separator comprises a polyolefin material and is formed as a laminate.

22. The battery of claim 16, further comprising a liquid electrolyte comprising at least one lithium salt dissolved in at least one non-aqueous solvent.

23. The battery of claim 16, wherein the first active material is provided on both sides of the positive electrode.

24. The battery of claim 16, wherein the positive electrode and the negative electrode are wound electrodes.

25. The battery of claim 16, wherein the lithium titanate material comprises $Li_4Ti_5O_{12}$.

26. The battery of claim 16, wherein the negative electrode further comprises a current collector that comprises copper.

27. A battery comprising:
a positive electrode and a negative electrode, the positive electrode comprising a $LiCoO_2$ active material and the negative electrode comprising $Li_4Ti_5O_{12}$ and $V_2O_5$ active materials;
a liquid electrolyte; and
a separator provided between the positive electrode and the negative electrode, wherein the separator comprises a polymeric material and includes pores for allowing the liquid electrolyte to pass through the separator.

28. The battery of claim 27, wherein the positive electrode and the negative electrode have zero voltage crossing potentials below a corrosion potential of a current collector of the negative electrode and above a decomposition potential of the $LiCoO_2$ active material.

29. The battery of claim 27, wherein the negative electrode comprises a current collector formed of a material selected from the group consisting of copper, titanium, aluminum, and nickel.

30. The battery of claim 27, wherein the separator comprises a polyolefin material formed as a laminate.

31. The battery of claim 27, wherein the liquid electrolyte comprises at least one lithium salt dissolved in at least one non-aqueous solvent.

32. The battery of claim 31, wherein the at least one lithium salt comprises $LiPF_6$ and the solvent comprises a mixture comprising ethylene carbonate and diethylene carbonate.

33. The battery of claim 27, wherein the battery has a capacity between approximately 10 mAh and 1000 mAh.

* * * * *